United States Patent
Al-Rashdan

(10) Patent No.: US 12,144,942 B2
(45) Date of Patent: Nov. 19, 2024

(54) SHEATHLESS GUIDE INTRODUCER

(71) Applicant: Ibrahim Al-Rashdan, Safat (KW)

(72) Inventor: Ibrahim Al-Rashdan, Safat (KW)

( * ) Notice: Subject to any disclaimer, the term of this patent is extended or adjusted under 35 U.S.C. 154(b) by 322 days.

(21) Appl. No.: 16/767,099

(22) PCT Filed: Nov. 26, 2018

(86) PCT No.: PCT/IB2018/059306
§ 371 (c)(1),
(2) Date: May 26, 2020

(87) PCT Pub. No.: WO2019/102429
PCT Pub. Date: May 31, 2019

(65) Prior Publication Data
US 2020/0376236 A1    Dec. 3, 2020

Related U.S. Application Data

(60) Provisional application No. 62/590,611, filed on Nov. 26, 2017.

(51) Int. Cl.
*A61M 25/06* (2006.01)
*A61M 29/02* (2006.01)
*A61M 25/00* (2006.01)

(52) U.S. Cl.
CPC ........ *A61M 25/0668* (2013.01); *A61M 29/02* (2013.01); *A61M 2025/0004* (2013.01);
(Continued)

(58) Field of Classification Search
CPC ...... A61M 2025/0004; A61M 25/0668; A61M 2025/0024; A61M 2029/025; A61M 29/02
See application file for complete search history.

(56) References Cited

U.S. PATENT DOCUMENTS

| 4,451,256 A | 5/1984 | Weikl et al. |
| 6,589,212 B1 * | 7/2003 | Navis ................ A61M 25/0017 |
| | | 604/164.01 |

(Continued)

FOREIGN PATENT DOCUMENTS

| WO | WO 01/34238 A1 | 5/2001 |
| WO | WO 2017/165298 A1 | 9/2017 |

OTHER PUBLICATIONS

International Search Report for corresponding International Application No. PCT/IB2018/059306 mailed on Mar. 1, 2019; 6 pages.
(Continued)

*Primary Examiner* — Deanna K Hall
(74) *Attorney, Agent, or Firm* — Winthrop & Weinstine, P.A.

(57) ABSTRACT

A system for inserting a guide catheter into a relatively small vessel may include an expandable introducer (100) configured for inserting into the vessel, expanding to dilate the vessel, and holding the vessel in an open condition. The system may also include a dilator (200) configured for arrangement within the introducer and for dilating the introducer. The expandable introducer may be removable from a catheter extending therethrough. A related method of introducing a catheter into a relatively small vessel may include inserting an introducer with a dilator arranged therein into the relatively small vessel, advancing the dilator within the introducer to split the introducer and dilate the vessel, removing the dilator, inserting a catheter through the dilated introducer and into the vessel, and removing the introducer from the catheter extending therethrough by splitting the introducer and removing laterally from the catheter. An introducer, alone, may also be provided.

14 Claims, 9 Drawing Sheets

(52) U.S. Cl.
   CPC . *A61M 25/0023* (2013.01); *A61M 2025/0024* (2013.01); *A61M 2029/025* (2013.01)

(56) References Cited

U.S. PATENT DOCUMENTS 10,898,690 B2 *  1/2021  Williams ............ A61M 25/065
   2006/0064124 A1   3/2006  Zhu et al.
   2014/0276927 A1   9/2014  Barker

OTHER PUBLICATIONS

Written Opinion for corresponding International Application No. PCT/IB2018/059306 mailed on Mar. 1, 2019; 10 pages.

* cited by examiner

SHEATHLESS GUIDE INTRODUCER

CROSS-REFERENCE TO RELATED APPLICATION

This application is a National Phase Application of PCT/IB2018/059306, filed on Nov. 26, 2018, which claims priority to U.S. Provisional Patent Application Ser. No. 62/590,611 filed on Nov. 26, 2017 and titled Expandable Sheath and System for Intravascular Insertion of a Medical Implement, the contents of which are hereby incorporated by reference herein in their entirety. A claim of priority to all, to the extent appropriate, is made.

TECHNICAL FIELD

The present disclosure relates to intravascular insertion of a medical device. More particularly, the present disclosure relates to intravascular insertion of a medical device in the radial artery or other relatively small vessel. Still more particularly, the present disclosure relates to a removable introducer for assisting in the intravascular insertion of a medical device in the radial artery of the wrist or other relatively small vessel.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cardiac procedures using an intravascular approach have become a common alternative to open-heart surgery. These procedures commonly involve efforts to open various coronary arteries that have become obstructed by cholesterol deposits. The intravascular approach may involve accessing the vasculature via the femoral artery and advancing a catheter to a problematic area. An expandable stent or other device may be advanced through the catheter and may be expanded against the wall of the artery to further open, re-open, or otherwise provide for proper or improved blood flow through the vasculature. Other procedures such as coronary angioplasty, coronary arteriography, cardiac catheterization, etc. may also rely on access to the vasculature via the femoral artery. While often sufficient, accessing the vasculature from the femoral artery is not without its drawbacks. For example, a relatively long catheter may be used due to the relatively long pathway from the thigh to the coronary region. Accordingly, efforts have been made to access coronary arteries via the radial artery in the wrist or lower arm of a patient. This approach involves a far shorter distance and a smaller percutaneous opening. However, the smaller size of the radial artery has proven difficult when inserting relatively large guides, catheters, and other devices.

SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In one or more embodiments, a system for inserting a guide catheter into a relatively small vessel may include an expandable introducer configured for inserting into the vessel, expanding to dilate the vessel, and holding the vessel in an open condition. The system may also include a dilator configured for arrangement within the introducer and for dilating the introducer. The expandable introducer may be removable from a catheter extending therethrough. In one or more embodiments, the introducer may be removable by splitting.

In one or more embodiments, a method of introducing a catheter into a relatively small vessel may include inserting an introducer with a dilator arranged therein into the relatively small vessel. The method may also include advancing the dilator within the introducer to split the introducer and dilate the vessel and removing the dilator. The method may also include inserting a catheter through the dilated introducer and into the vessel. The method may further include removing the introducer from the catheter extending therethrough by splitting the introducer and removing laterally from the catheter.

In one or more additional embodiments, an introducer for inserting a guide catheter into a relatively small vessel may include a distal tip, a dilating portion arranged proximal to the distal, and a hub arranged adjacent and proximal to the dilating portion. The hub may include a removal feature configured to split the hub and allow removal of the introducer from a catheter extending therethrough.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure, in one or more embodiments, relates to a system for introducing a guide catheter to the radial artery or other relatively small artery. The system includes an introducer that is sized and shaped for accessing the small vasculature after which it may be dilated to expand the available space within the artery for the guide catheter. The guide catheter may, thus, be more easily inserted and advanced within the relatively small vasculature. Moreover, after the guide catheter is in place, the introducer may be removed. The removal of the guide catheter is unique because the introducer is arranged concentrically around the guide catheter, which would commonly mean that the introducer would need to be backed all the way off of the proximal end of the catheter. However, the present design allows for lateral removal of the introducer providing for a sheathless use of the guide catheter once inserted and also allowing for a catheter that is free of obstructions or other devices outside of the patient. The guide catheter may then be used for one of several cardiovascular or other procedures.

Figure 1:
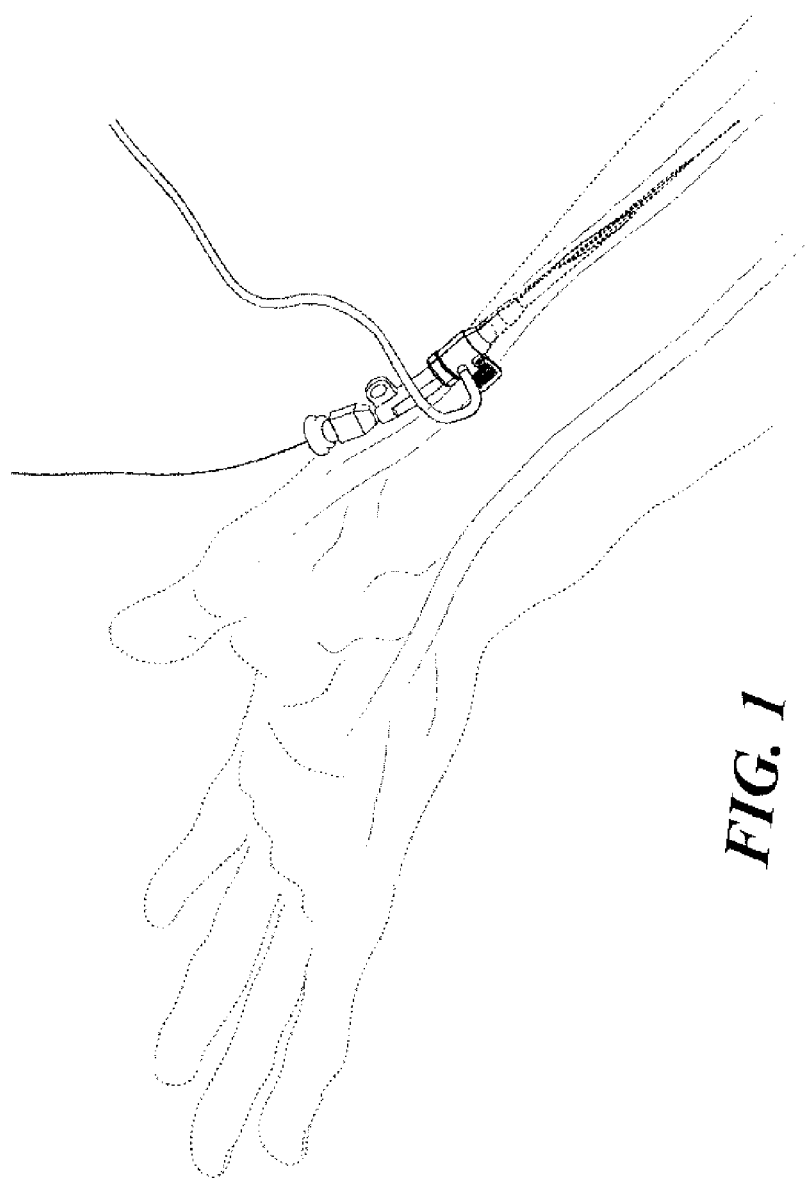
FIG. 1 is a perspective view of an introducer, a dilator, and a stop collar arranged to extend into a radial artery of a patient, according to one or more embodiments.

FIG. 1 shows a guide catheter delivery system in place in the radial artery of a patient's wrist or forearm. The system may be configured to allow for easier access to relatively small vasculature by being easily inserted and by expanding the artery to receive more sizable devices. As shown, the system may include a guide wire 50, an introducer 100, a dilator 200, and a dilation control collar 31. The relatively narrow distal tips of the dilator and the introducer may allow for insertion into the small vasculature and the dilator may be used to expand the introducer so as to hold the vasculature open. The dilator may then be removed and the introducer may hold the vasculature open while a guide catheter is inserted and then the introducer may be removed. The system may, thus, allow for insertion of a guide catheter into a vessel that would otherwise not be able to receive such a size of a guide catheter or would at least cause insertion of the guide catheter to be difficult.

Figure 2:
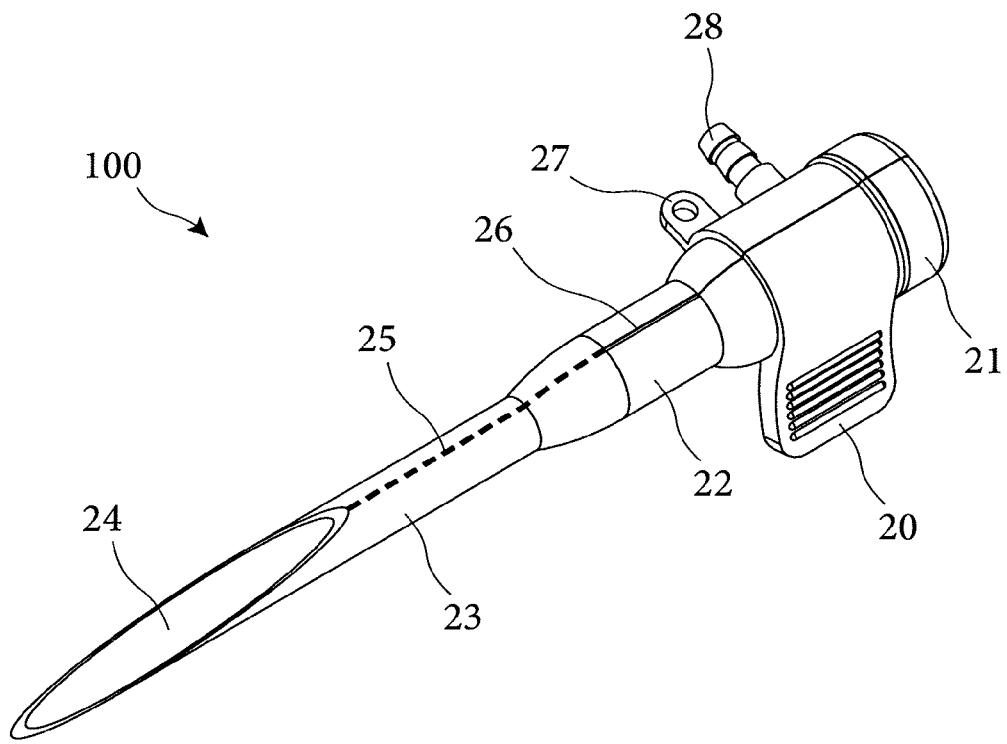
FIG. 2 is a front and top perspective view of the introducer of FIG. 1, according to one or more embodiments.
Figure 3:
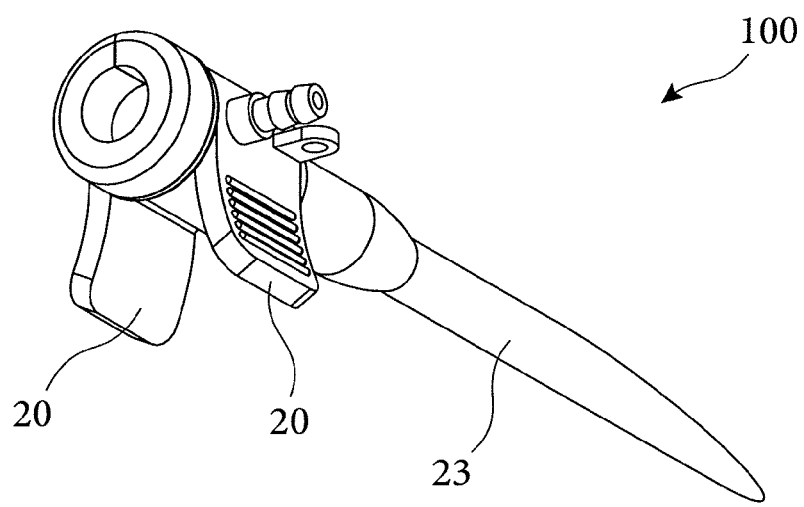
FIG. 3 is a rear and bottom perspective view of the introducer of FIG. 1, according to one or more embodiments.

FIG. 2 shows a perspective front or distal and side view of the introducer portion 100 of the system. The introducer 100 may be configured for ease of insertion into relatively small vasculature, expansion of the vasculature, holding the vasculature open to receive a guide catheter, and removal from the patient when the guide catheter is in place. The introducer 100 may include a hub 20, a hold open portion 22, a transition portion, a body portion 23, and a distal tip 24. The several portions of the introducer 100 may perform particular functions while forming smaller portions of an otherwise integral or unitary device. FIG. 3 shows a perspective rear or proximal and side view of the introducer 100.

With reference to FIGS. 1-3 and 11, the distal tip 24 of the introducer 100 may be described. The distal tip 24 may include a substantially flat and narrow point at its distal most end, which may form a substantially knife-tip shape. The distal tip 24 may expand laterally as it extends in the proximal direction from the point and may include an increasingly semicircular shape when viewed in cross-section. At the most proximal portion, the distal tip 24 may include a substantially fully circular shape when viewed in cross-section. The shape of the distal tip 24 may be formed by, for example, beveling or chamfering an otherwise tubular element. The bevel or chamfer may include a substantially shallow angle of attack relative to a longitudinal axis of the tubular element so as to create a relatively long distal tip. The wall of the tubular member may form an elliptical shape along the bevel or chamfer and when viewed from above as shown in FIG. 2. The distal end of the elliptical shape may be the point of the distal tip and the proximal end of the elliptical shape may form the proximal most portion of the distal tip where the distal tip transitions to the body portion. In one or more embodiments, the distal tip may include an inner diameter of approximately 2-10 Fr. or approximately 4-8 Fr. or approximately 6 Fr. The distal tip may have a length ranging from approximately 1-6 cm, or from approximately 2-5 cm, or from approximately 3-4 cm. The distal tip may include a suitable material thickness selected based on the material type and to provide for a relatively stiff tubular structure while allowing for relatively easy tearing of the material when perforated. In one or more embodiments, the material thickness of the distal tip and the body portion may be approximately 25% of the thickness of the hole open portion to allow for tearing of the material.

The body portion 23 may be arranged proximal or immediately proximal to the distal tip. The body portion 23 may include a substantially tubular element having an inner diameter matching that of the distal tip. The body portion 23 may have a length ranging from approximately 1-6 cm, or from approximately 2-5 cm, or from approximately 3-4 cm. The body portion may include a perforated sidewall. The perforated sidewall may include a plurality of perforations 25 extending along a substantially straight line beginning at the proximal end of the elliptical shape. The line of perforations 25 may extend proximally along the full length of the body portion 23 and may continue into the transition portion. The line of perforations 25 may extend generally parallel to an axis of the body portion. Alternatively, the line of perforations may form a spiral shape. The body portion may include a material thickness that is the same or similar as that of the distal tip and, as mention, in one or more embodiments, the thickness of the body portion and the distal tip may be substantially thinner than the hold open portion.

The transition portion may be arranged proximal or immediately proximal to the body portion. The transition portion may be configured for transitioning between varying outer diameters and varying inner diameters. For example, the hold open portion 22 may have an outer diameter greater than the outer diameter of the body portion 23 and the transition portion may provide for a transition between these two diameters. In one or more embodiments, the transition portion may have a substantially conical outer surface with an outer diameter at its distal end that is substantially equal to the body portion 23 and an outer diameter at its proximal end that is substantially equal to the hold open portion 22. In one or more embodiments, the outer surface of the transition portion may create a substantially straight transition. In other embodiments, the outer surface may be slightly convex along a line extending from the body portion 23 to the hold open portion 22, as shown, or the outer surface may be slightly concave along such a line. All of the above shapes may be considered substantially conical. The line of perforations 25 on the body portion 23 may continue through the transition portion and, as such, the perforation in the transition portion may be in substantial alignment with the line of perforations 25 in the body portion 23. The material thickness of the transition portion may be the same or similar to the thickness of the body portion and the inner diameter of the transition portion may track with the outer diameter taking the thickness of the material into account. In other embodiments, the wall thickness may vary along the length of the transition portion allowing the inner and outer surfaces of the transition portion to be different. The transition portion may have a length ranging from approximately 0.25-2 cm or approximately 0.5-1 cm or approximately 0.75 cm.

The hold open portion 22 may be arranged proximal or immediately proximal to the transition portion. The hold open portion 22 may include a substantially tubular element having an inner diameter ranging from approximately 3 Fr. to 10 Fr. or from approximately 5 Fr. to 7 Fr. or approximately 6 Fr. The hold open portion 22 may have a length ranging from approximately 0.5-6 cm, or from approximately 1-4 cm, or from approximately 2-3 cm. The hold open portion 22 may include a perforated sidewall. The perforated sidewall may include a plurality of perforations 26 extending along a substantially straight line beginning at the distal end and extending to the proximal end generally parallel to the axis of the hold open portion 22. The line of perforations 26 may extend along the full length of the hold open portion 22 and may continue into the hub 20. The line of perforations on the hold open portion 22 may be aligned with the line of perforations along the transition portion. The hold open portion may include a material thickness that is the same or similar as that of the distal tip, the body portion, and/or the transition portion. In one or more embodiments, the hold open portion may be slightly thicker. Moreover, in one or more embodiments, the perforation 26 may include a continuous divide or separation line rather than isolated perforation holes. Alternatively or additionally, the continuous divide or separation may be a reduction in material thickness ranging from approximately 50%-95% or from approximately 60%-80% or approximately 75%. In the latter case, the material thickness at the separation may be approximately 25% of the hold open portion thickness and, as such, may match the thickness of the body portion and the distal tip.

The hub 20 may be arranged proximal to or immediately proximal to the hold open portion 22 of the introducer. The hub may be configured for delivering fluids to the vessel of the patient, for receiving the dilator, for secured attachment to the skin of a patient, and for controlling the removal of the introducer. The hub may include a distal nose, a central portion, and a proximal collar 21. The hub 20 may also include an anchoring device 27, a fluid port 28, and a breakaway element.

The distal nose may be configured for arresting the advancement of the introducer 100 and, as such, may form a relatively abrupt transition from the hold open portion 22 to the larger diameter central portion of the hub. The distal nose may have a convex surface adapted to form the vessel opening into a flare or bell shape, for example. The central portion of the hub may be generally tubular in shape and may form a body on which a plurality of other features may be mounted and interact. The hub may include an outer diameter much larger than the hold open portion 22 and may allow the user to grasp the introducer and control its position, for example. The proximal collar 21 may be arranged on the proximal end of the hub 20 and may form the proximal most end of the introducer 100. The proximal collar 21 may be configured for abutment with the dilator 200 and may include a substantially flat annular abutment surface on its proximal face. The proximal collar may have an outer diameter slightly larger than the central portion of the hub and it may be sized to suitably stop advancement of the dilator 200.

All of the portions of the hub (i.e., the distal nose, the central portion, and the proximal collar) may include a perforation allowing for separation of the otherwise continuous tubular structure. The perforation may extend along a substantially straight line from the distal nose, through the central portion, and through the proximal collar. The perforation may include perforation holes or the perforation may include a generally continuous divide. Like the hold open portion, the divide may include a weakened or thinned area where the thickness is reduced to allow for tearing of the device. The thickness at the divide may be the same or similar to the thickness of the divide in the hold open portion.

One or more additional features may be attached to and/or form a portion of the hub 20. As shown, an anchoring device 27 may extend laterally away from the surface of the hub at the central portion, for example. The anchoring device 27 may be an ear or tab with an eye for receiving a stitch or other fastener or a tie, for securing the introducer to the skin of a patient, for example. The hub may also include a port 28 configured for connection of fluid systems to allow for the delivery of fluids to the hub and into the vessel. The fluid port 28 may include a nipple or hose barb, for example, allowing for tubing to be connected to the hub. In one or more embodiments, the tubing may be part of a hemostasis valve assembly or another fluid delivery and control system may be provided.

As shown and mentioned, the hub 20 may also include a breakaway element. The breakaway element may be configured for splitting the hub open along the perforation line allowing it to be removed when a guide catheter is positioned through the introducer. In one or more embodiments, the breakaway element may include a pair of opposing levers. The levers may extend generally tangentially away from the surface of the hub and may be substantially rigid elements that are substantially rigidly secured to the hub. In one or more embodiments, for example, the levers may be formed integrally with the hub such as through an injection molding process. The levers may be substantially thick elements having a thickness that is the same or similar to the thickness of the hub wall. The hub wall may be substantially continuous around the periphery of the hub including where the levers extend therefrom and including the space between the levers. The portion of the hub wall between the levers may form a compression element forming a fulcrum for the levers. As such, when the levers are pressed toward one another, they may be held stationary relative to one another by the fulcrum. As the outer tips of the levers approach one another, the levers may stretch, pull, or tear the opposing side of the hub wall open along the perforation line allowing the hub to be removed from a guide catheter or other longitudinal element extending therethrough, for example. The levers may extend away from the hub and may have a slightly curved shape opposite the curvature of the hub and forming a substantially concave grasping surface on an outer part thereof. The grasping surface may include a series of burs, bumps, grooves, or protruding lines forming a gripping feature on the surface of the levers.

Figure 4:
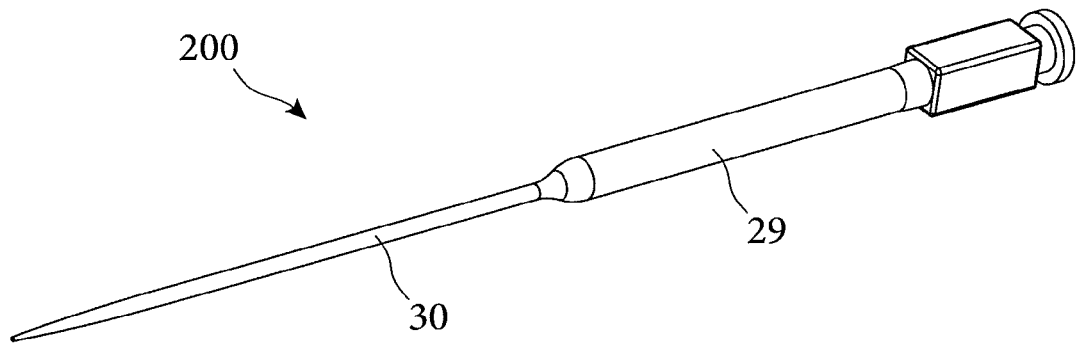
FIG. 4 is a perspective view of the dilator of FIG. 1, according to one or more embodiments.

The dilator 200 is shown in FIG. 4. The dilator 200 may be configured for insertion into the proximal end of the introducer 100 and may be used to dilate the distal tip 24, body portion 23, and transition portion of the introducer 100. The dilator 200 may include a generally elongate element having a leading tip 30, a dilating transition, and a trailing shaft 29. The dilator 200 may also include a handle portion with a thumb press. The entirety of the dilator may include an inner lumen configured for receiving a guide wire such that the dilator may be advanced over a guide wire and into a patient's vessel.

The leading tip 30 may be substantially elongate with a relatively narrow point. The leading tip 30 may be round in cross-section and may have an outer diameter smaller than the inner diameter of the distal tip and body portion of the introducer. As such, the leading tip 30 may be readily advanced through the introducer 100 and may be used to assist with insertion of the introducer 100. The leading tip 30 may have a length ranging from approximately 1-6 cm, or approximately 2-4 cm, or the leading tip may be approximately 3 cm long.

The dilating transition may be configured for engaging the transition portion of the introducer 100 and for splitting the body portion 23 and the transition portion of the introducer along the perforation line 25. The dilating transition may include a relatively abrupt transition in the outer diameter of the dilator between the leading tip 30 and the trailing shaft 29. The dilating transition may include a concave cone shape leading to a convex cone shape creating a relatively blunt nose for engaging the transition portion of the introducer 100. The blunt nature of the nose may provide for a relatively abrupt splitting of the body portion 23 and the transition portion of the introducer 100 when the dilator is advanced therein providing for tactical feedback when the introducer is split. The convex cone shape portion of the dilating transition may be the same or similar to the inner shape of the transition portion of the introducer 100 allowing the dilating transition to seat in the introducer upon advancement of the dilating transition into the introducer.

The trailing shaft 29 of the dilator 200 may be configured to maintain the body portion 23 and the transition portion of the introducer 100 in the dilated condition as the dilating transition is advanced through them. That is, as the dilating transition is advanced passed the transition portion and into the body portion 23 of the introducer 100, the trailing shaft 29 may follow behind holding these portions of the introducer 100 in the dilated condition. The trailing shaft 29 may be substantially tubular in shape and may have an outer diameter substantially the same as the largest diameter of the dilating transition. In one or more embodiments, this diameter of the trailing shaft may be substantially the same or slightly larger than the hold open portion of the introducer (e.g., 8 Fr) The trailing shaft 29 may also have a length that is the same, similar, or slightly longer than the combined lengths of the body portion 23, the transition portion, the hold open portion 22, and the hub 20 such that when the dilator 200 is inserted into the introducer 100, the distal end of the trailing shaft 29 reaches the distal tip 24 of the introducer 100.

As mentioned, the dilator 200 may also include a handle portion and a thumb press. The handle portion may be adapted to for gripping and/or handling by the user and for abutting engagement with the collar on the introducer. In one or more embodiments, the handle portion may be substantially rectangular for easy gripping by the user. Alternatively or additionally, the handle portion may include finger depressions for better or increased gripping. The handle portion may include a proximal abutting surface adapted to abut the collar 21 on the introducer 100. The handle portion may be sized larger than the trailing shaft 29 so as to form the abutting surface. The abutting surface may be substantially flat to provide a clear contact indication and a stop when the dilator 200 is fully inserted into the introducer. The thumb press may be arranged at the proximal end of the handle and may include a substantially flat, concave, or other shaped surface for receiving pressure from a thumb or other finger of the user such that the dilator 200 may be advanced into the introducer 100 and/or such that the dilator 200 may be used to advance the introducer 200.

Figure 5:
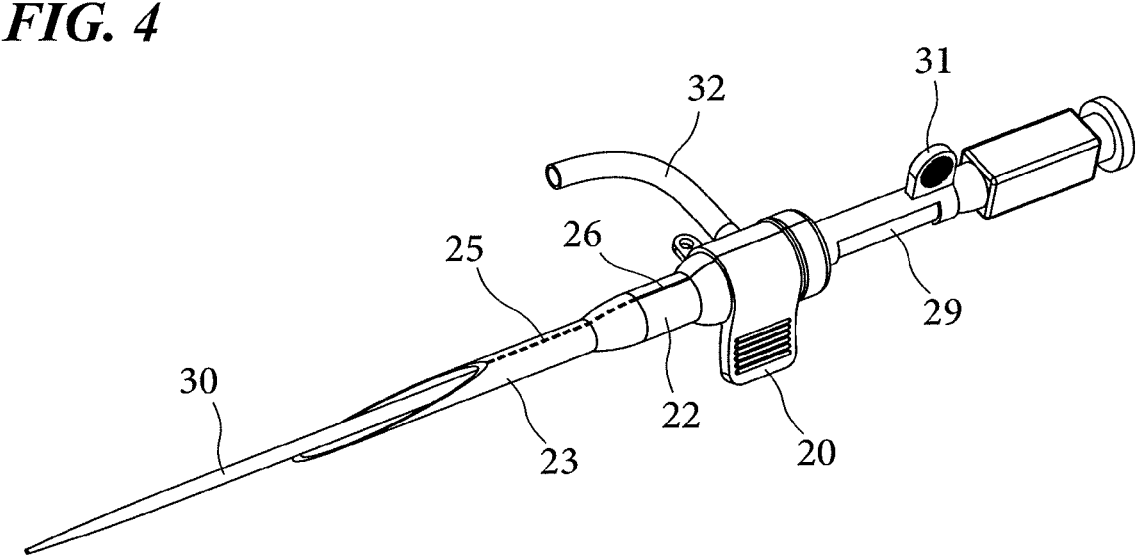
FIG. 5 is a perspective view of the dilator, the introducer, and the stop collar of FIG. 1, according to one or more embodiments.
Figure 6:
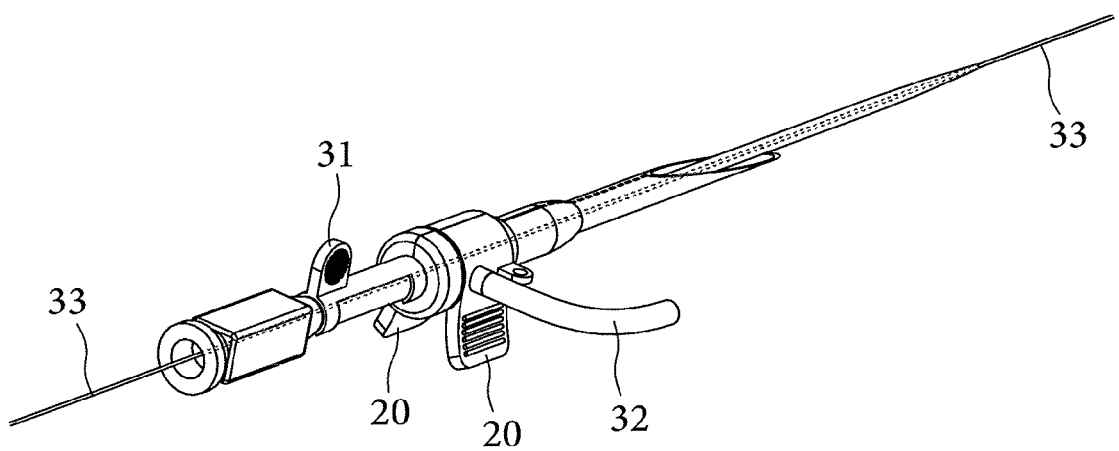
FIG. 6 is a perspective view of the dilator, the introducer, and the stop collar of FIG. 1 arranged on a guide wire, according to one or more embodiments of the present disclosure.
Figure 7:
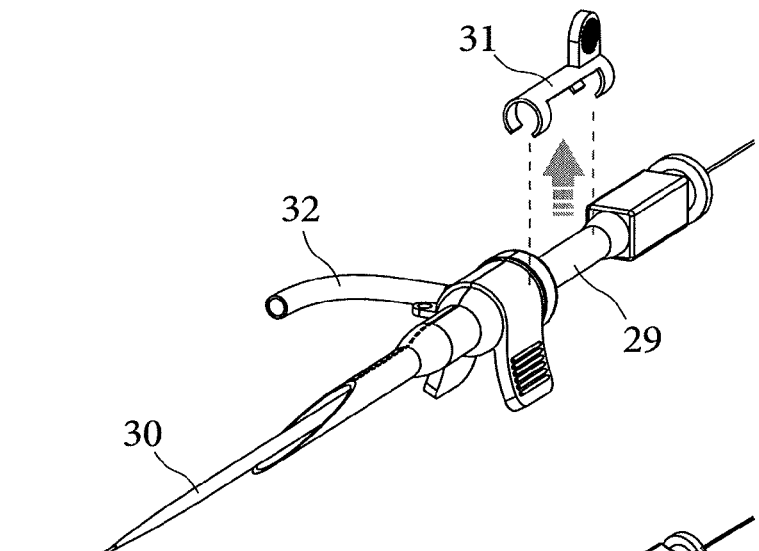
FIG. 7 is a perspective view of the dilator and the introducer and depicting removal of the stop collar, according to one or more embodiments.
Figure 8:
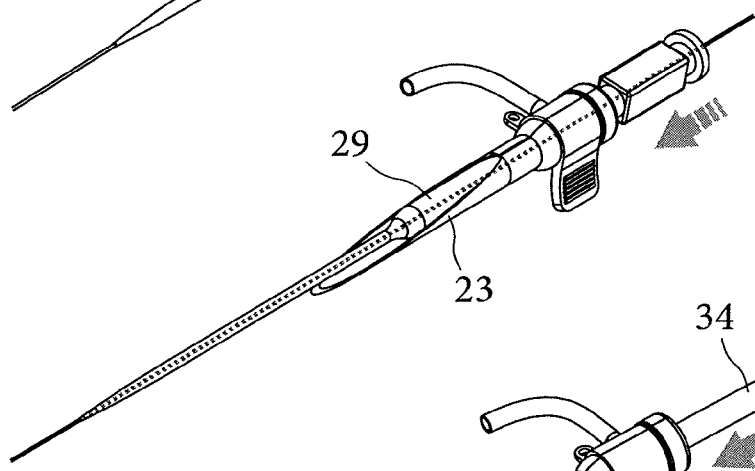
FIG. 8 is a perspective view of the dilator and the introducer and depicting advancement of the dilator without the stop collar in place, according to one or more embodiments.
Figure 9:
FIG. 9 is a perspective view of a guide catheter advanced through the introducer, according to one or more embodiments.
Figure 10:
FIG. 10 is a perspective view of a guide catheter depicting removal of the introducer, according to one or more embodiments.
Figure 10:
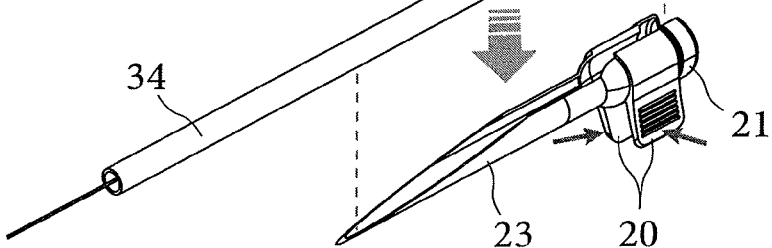

As shown in FIGS. 5-7, a standoff 31 may be provided. The standoff 31 may be configured to resist or otherwise control the amount of advancement of the dilator 200 relative to the introducer 100. As shown, the standoff 31 may be configured for arrangement on the trailing shaft 29 of the dilator 200. The standoff 31 may include a strut portion, a clamping portion, and a removing feature. The strut portion may include compressive element configured for resisting compressive forces between the dilator and the introducer. As shown, the strut portion may be an elongate portion having a radiused shape when viewed in cross-section looking along the longitudinal axis. As such, the strut portion may be configured for nesting engagement with the trailing shaft 29 of the dilator 200. The relatively thin elongate nature of the strut portion may be strengthened by the radius-shaped cross section. The clamping portion may include one or more pairs of spring clamps configured for removably engaging the trailing shaft 29 of the dilator 200. As shown, the spring clamps may include curved tabs that extend off of the strut portion around the trailing shaft 29. The spring clamps may function in pairs and have opposing clamping forces that grip the trailing shaft between them. The spring clamps may be flexible so as to be removable from the trailing shaft when pulled with sufficient force to overcome the clamping force and allow removal of the standoff. The pulling force may be imparted to the standoff by a user using the removing feature. The removing feature may include a pull tab, for example, extending from the strut in a direction opposite that of the clamping portion. The pull tab may be relatively thin and may include gripping surfaces on opposing surfaces to allow for a thumb and forefinger, for example, to grip the standoff and pull it off of the dilator.

In one or more alternative embodiments, the standoff may include levers 98 similar to the levers described with respect to the hub 20 of the introducer 100. That is, as shown in FIG.

Figure 16:
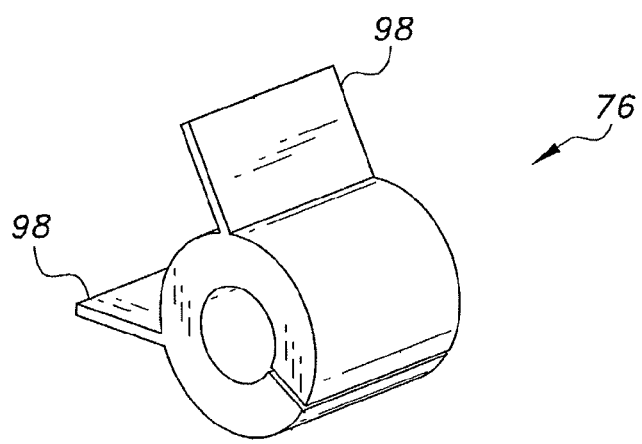
FIG. 16 shows yet another alternative embodiment of a standoff, according to one or more embodiments.
Figure 17A:
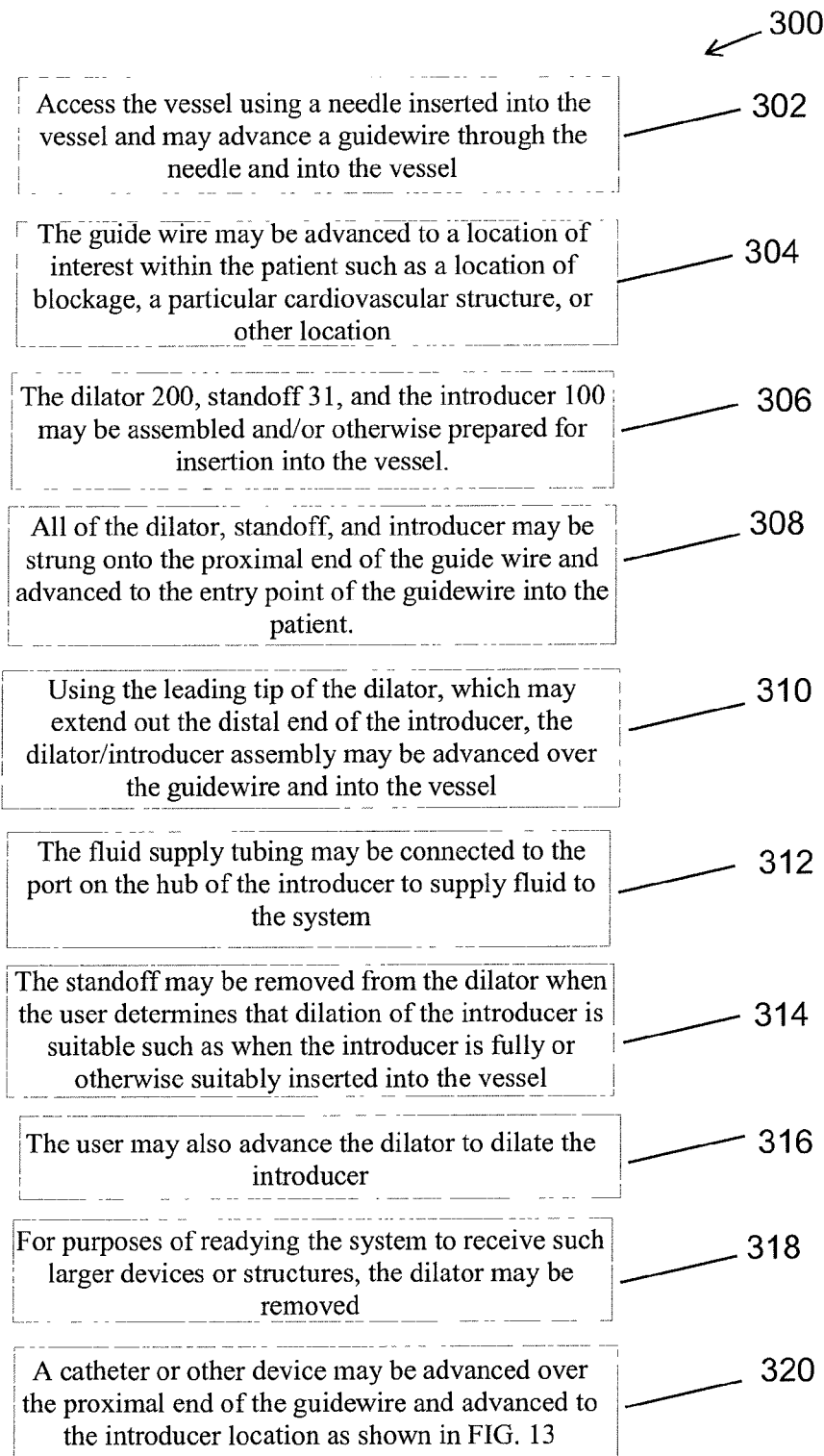
FIG. 17A shows a method of use of the system, according to one or more embodiments.
Figure 17B:
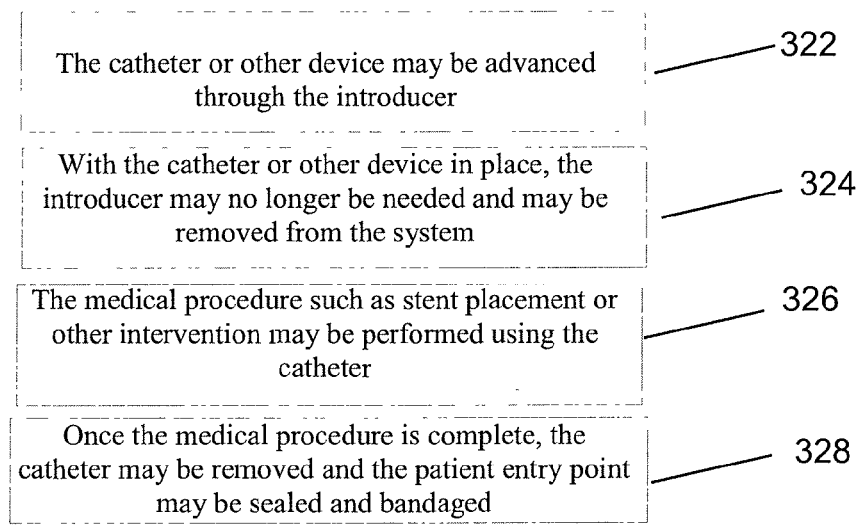
FIG. 17B is a continuation thereof.

15, a plurality of pry open levers 98 may be provided, where the levers reach around the standoff 60 and function to pry open one side of the standoff 60 to allow removal of the standoff. Alternatively, as shown in FIG. 16, the levers 98 may be more akin to the levers described for the hub 20. That is, as shown in FIG. 16, the levers 98 may extend laterally from the standoff 76 creating a fulcrum between them and allowing the levers 98 to be squeezed or otherwise brought together to open the opposing side of the standoff 76 allowing for removal thereof.

With reference to FIGS. 7-10 and in short, the dilator 200 and the introducer 100 may be assembled outside of the patient by inserting the dilator 200 into the introducer 100. The combined devices may be advanced into the patient and the handle portion and thumb press, for example, may be used to advance the system. Once properly positioned, the standoff 31 may be removed and the dilator 200 may be more fully advanced into the introducer 100 thereby dilating the body portion 23 and the transition portion. The dilator 200 may then be removed and a guide catheter 34 may be advanced within the introducer 100 and into the patient. The introducer 100 may then be removed from the patient and also broken open with the levers and removed from the guide catheter 34 to free the system of used, bothersome, or otherwise unneeded devices allowing the procedure to continue unhindered by such elements.

A more detailed discussion of the method of use 300 may be with respect to FIGS. 11-14 and FIGS. 17A and 17B. Initially, and while not shown, a nurse, doctor, other medical provider, or other user may locate the radial artery or other vessel of a patient using common techniques. The user may access the vessel using a needle inserted into the vessel and may advance a guidewire through the needle and into the vessel. (302) The needle may be removed by sliding it off of a proximal end of the guidewire. The guide wire may be advanced to a location of interest within the patient such as a location of blockage, a particular cardiovascular structure, or other location. (304) At this point, the patient may be ready to receive a guide catheter to deliver devices to address a particular medical indication, but the small vasculature may not allow for readily inserting such devices. As such, the system of the present application may be used to further prepare the patient for such insertion.

Figure 11:
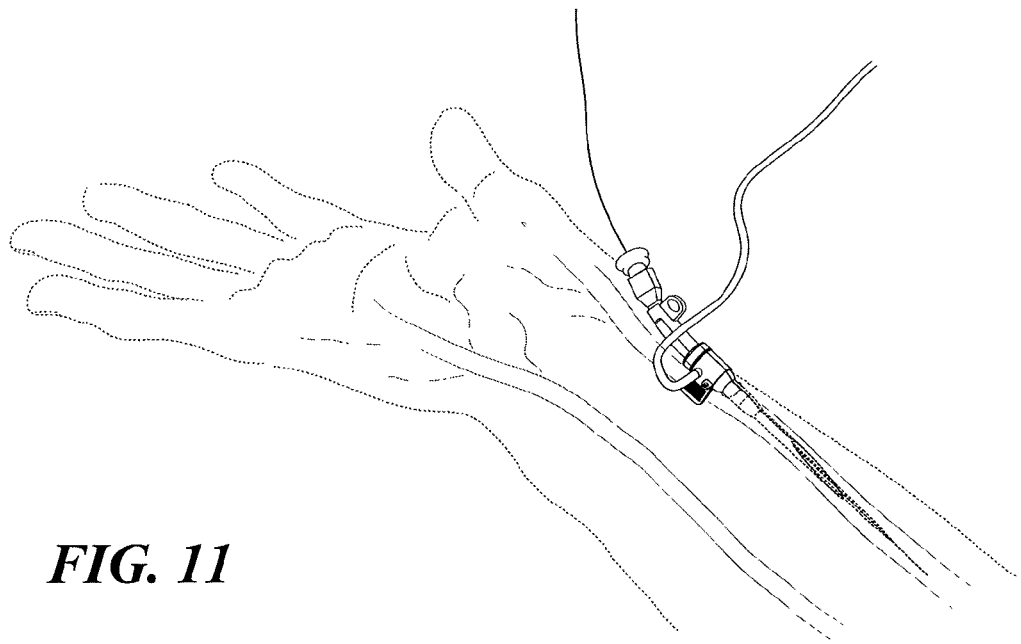
FIG. 11 depicts an initial step of accessing the vasculature with the introducer, dilator, and stop collar, via the radial artery, according to one or more embodiments.

The dilator 200, standoff 31, and the introducer 100 may be assembled and/or otherwise prepared for insertion into the vessel. (306) For example, the standoff 31 may be clamped onto the trailing shaft 29 of the dilator 200 and the dilator 200 may be inserted into a proximal end of the introducer 100 up to a point where a distal end of the standoff 31 engages the abutting surface of the collar 21 on the hub 20 of the introducer 100. All of the dilator, standoff, and introducer may be strung onto the proximal end of the guide wire and advanced to the entry point of the guidewire into the patient. (308) Using the leading tip of the dilator, which may extend out the distal end of the introducer, the dilator/introducer assembly may be advanced over the guidewire and into the vessel. (310) The assembly may be inserted to a point as shown in FIG. 11. For example, the assembly may be advanced such that the distal tip, the body portion, the transition portion, and all or a portion of the dilating portion of the introducer are positioned within the vessel of the patient. The leading tip of the dilator may allow for easy entry into the vessel and the distal tip may be snugly nested on the leading tip of the dilator. As such, and as the system is advanced into the vessel, the distal tip of the introducer may relatively easily enter the vessel. Moreover, during insertion, the standoff may control the advancing motion of the dilator relative to the introducer so as to avoid premature dilation of the introducer until the introducer is suitably arranged within the vessel. As also shown, fluid supply tubing may be connected to the port on the hub of the introducer to supply fluid to the system. (312)

Figure 12:
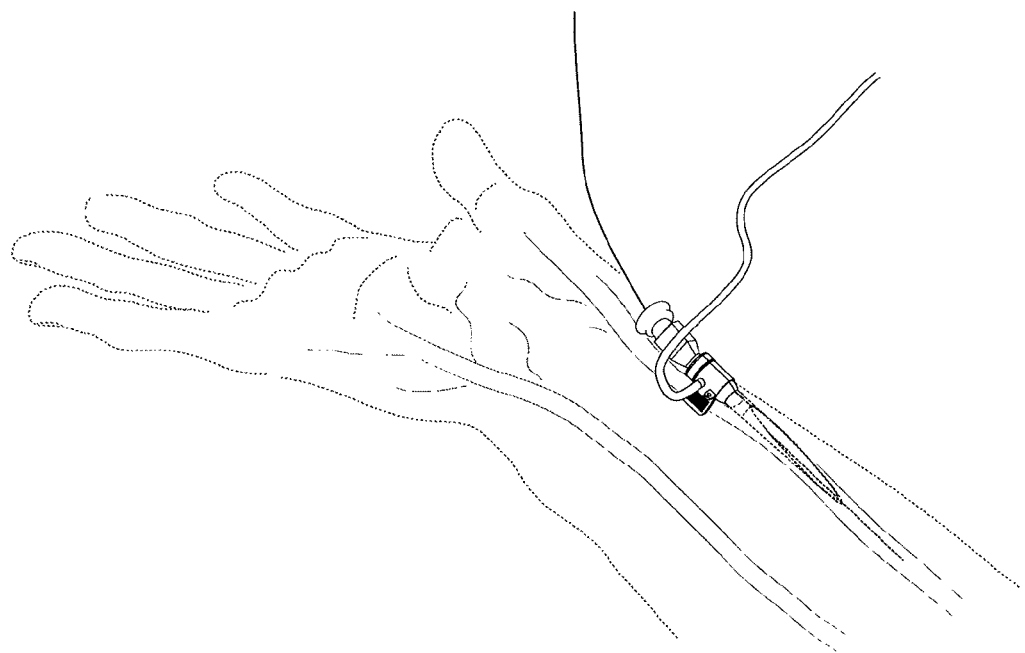
FIG. 12 depicts advancement of the dilator with the stop collar removed or omitted, according to one or more embodiments.

The introducer may have been inserted into the patient, but the system may not be fully prepared to receive a guide catheter or other device because the distal tip, body portion, and transition portion may remain too narrow or small to receive such a device. Accordingly, the standoff may be removed from the dilator when the user determines that dilation of the introducer is suitable such as when the introducer is fully or otherwise suitably inserted into the vessel. (314) A user may remove the standoff by grasping the tab and pulling the standoff to remove the clamping portion from trailing shaft of the dilator and allowing the standoff to be removed in a lateral direction. The user may also advance the dilator to dilate the introducer. (316) For example, the user may grip the handle portion of the dilator and press the dilator forward while also gripping the hub of the introducer thereby preventing further advancement of the introducer under the advancing force of the dilator. The user may press the dilator forward relative to the introducer causing the dilating transition of the dilator to break through the transition portion of the introducer and breaking/tearing the perforations on the transition portion of the introducer. The dilator may be further advanced into and through the introducer such that the dilating transition of the dilating portion continues to split the introducer along the perforation line on the body portion of the introducer while the trailing shaft trails behind maintaining the parts in their dilated condition. The dilator may continue to be advanced until the abutting surface on the handle portion of the dilator abuts the abutting surface on the collar of the hub of the introducer as shown in FIG. 12.

At this point, the introducer has been inserted into the relatively small vasculature and has been used to expand the vasculature to allow for larger devices or structures to more easily be inserted into the vasculature. For purposes of readying the system to receive such larger devices or structures, the dilator may be removed. (318) For example, the dilator may be moved proximally out of the introducer while holding the introducer in place. The dilator may be removed from the system by backing it off of a proximal end of the guidewire.

Figure 13:
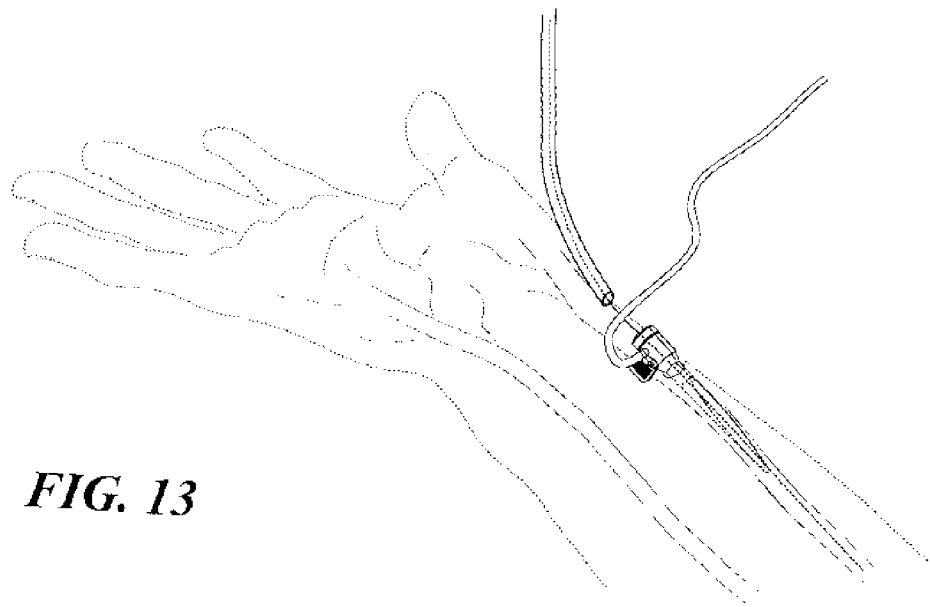
FIG. 13 depicts advancement of the guide catheter along the guidewire toward the proximal end of the dilator, according to one or more embodiments.
Figure 14:
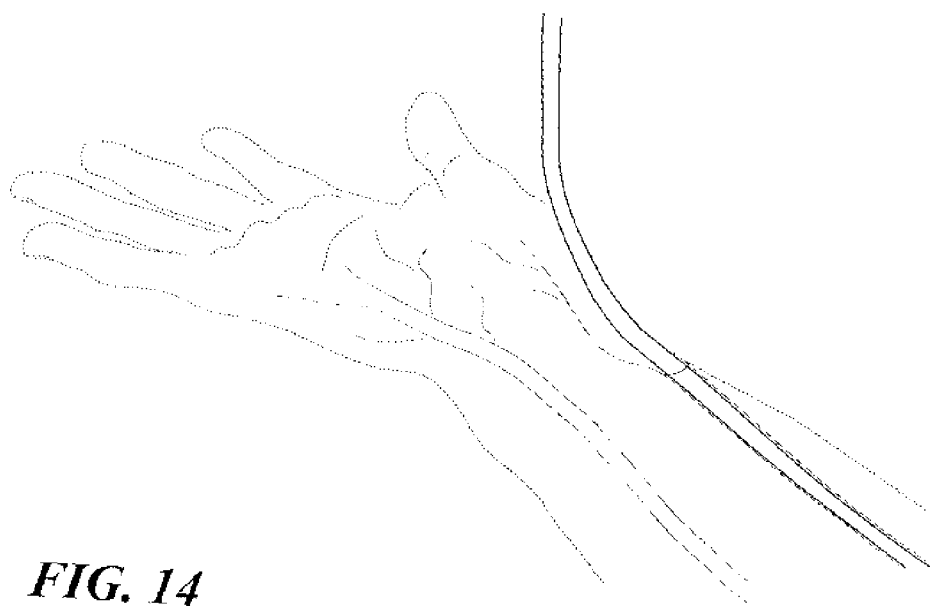
FIG. 14 depicts the guide catheter in place without the introducer, according to one or more embodiments.
Figure 15:
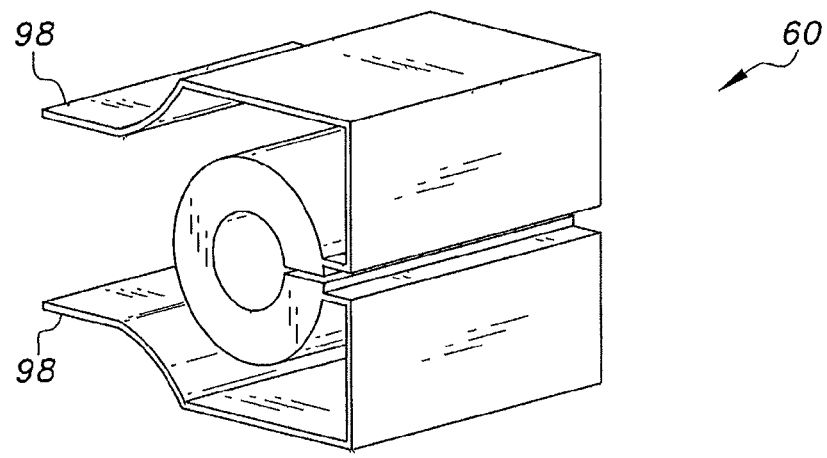
FIG. 15 shows an alternative embodiment of a standoff, according to one or more embodiments.

A catheter or other device may be advanced over the proximal end of the guidewire and advanced to the introducer location as shown in FIG. 13. (320) The catheter or other device may be advanced through the introducer. (322) Where the introducer has collapsed or otherwise returned to its pre-dilated condition, the catheter may rely on the introducer as a wedge, so to speak, to press the vessel wall outward to receive the leading tip of the catheter. The catheter may be advanced through the introducer into the vasculature and along the guidewire to the medical indication point needing to be addressed. With the catheter or other device in place, the introducer may no longer be needed and may be removed from the system. (324) For example, the introducer may be moved proximally along the catheter and out of the patient and the levers on the hub of the introducer may be used to break open the introducer and remove it laterally from the system. That is, the levers may be squeezed together, thereby pivoting about the fulcrum between them causing the opposite side of the hub to split open allowing the catheter to pass through the gap in the sidewall of the introducer and allowing the introducer to be removed from the side. This may leave a relatively clean insertion of the catheter into the small vasculature without the presence of a sheath or other extraneous devices hanging on the catheter outside the patient as shown in FIG. 16. The medical procedure such as stent placement or other intervention may be performed using the catheter. (326) Once the medical procedure is complete, the catheter may be removed and the patient entry point may be sealed and bandaged. (328)

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A system for inserting a guide catheter into a relatively small vessel, the system comprising:

an expandable introducer configured for inserting into the vessel, expanding to dilate the vessel, and holding the vessel in an open condition, wherein the introducer includes a body portion having a plurality of perforations, wherein, prior to perforating the perforations, the body portion comprises a continuous tubular structure; and a dilator configured for arrangement within the introducer and for dilating the introducer, wherein the dilator expands the introducer by breaking the perforations;

wherein the expandable introducer is removable from a catheter extending therethrough.

2. The system of claim 1, further comprising a hub having a perforated sidewall, wherein the hub is arranged proximal to a hold open portion of the introducer.

3. The system of claim 2, wherein the hub comprises a pair of opposing levers for splitting the perforated sidewall of the hub to open the hub open for removal.

4. The system of claim 3, wherein the levers extending generally tangentially from the perimeter of the hub.

5. The system of claim 1, further comprising a standoff for maintaining the dilator and the introducer in offset relative positions.

6. The system of claim 1, wherein the introducer comprises a relatively narrow distal tip and a transition portion.

7. The system of claim 6, wherein the distal tip comprises a chamfered tip having a flat knife-shaped distal end.

8. The system of claim 7, wherein the chamfered tip forms an elliptical shape.

9. The system of claim 1, wherein the expandable introducer further comprises a transition portion and the perforations extend in a line along the body portion and the transition portion.

10. The system of claim 1, wherein the plurality of perforations extend along a full length of the body portion.

11. A method of introducing a catheter into a relatively small vessel, comprising:

inserting an introducer with a dilator arranged therein into the relatively small vessel, wherein the introducer includes a body portion having a plurality of perforations, wherein, prior to perforating the perforations, the body comprises a continuous tubular structure;

advancing the dilator within the introducer to split the introducer along the plurality of perforations to break the perforations and expand the introducer and dilate the vessel;

removing the dilator;

inserting a catheter through the dilated introducer and into the vessel;

removing the introducer from the catheter extending therethrough.

12. The method of claim 11, wherein inserting the introducer comprises advancing the dilating portion of the introducer to within the vessel.

13. The method of claim 12, wherein the introducer and dilator are arranged on a guidewire for insertion into the vessel.

14. The method of claim 11, wherein a standoff is arranged on the dilator for controlling the relative advancement of the dilator relative to the introducer.

* * * * *